United States Patent
Linnonmaa et al.

(10) Patent No.: US 6,749,888 B2
(45) Date of Patent: Jun. 15, 2004

(54) METHOD AND APPARATUS FOR DETERMINING THE PROFILE OF A COATING LAYER

(75) Inventors: Jukka Linnonmaa, Gladstone (FI); Vilho Nissinen, Numminen (FI); Jukka T. Mäkinen, Kerava (FI); Jouni Raki, Espoo (FI); Pasi Rajala, Järvenpää (FI); Jari-Matti Karjanmaa, Hyvinkää (FI)

(73) Assignee: Metso Paper, Inc., Helsinki (FI)

( * ) Notice: Subject to any disclaimer, the term of this patent is extended or adjusted under 35 U.S.C. 154(b) by 0 days.

(21) Appl. No.: 10/130,553

(22) PCT Filed: Dec. 11, 2000

(86) PCT No.: PCT/FI00/01083
§ 371 (c)(1),
(2), (4) Date: Aug. 7, 2002

(87) PCT Pub. No.: WO01/42773
PCT Pub. Date: Jun. 14, 2001

(65) Prior Publication Data
US 2003/0108661 A1 Jun. 12, 2003

(30) Foreign Application Priority Data
Dec. 9, 1999 (FI) .................................. 992652

(51) Int. Cl.[7] .......................... B05D 1/00; B05C 11/00
(52) U.S. Cl. .................... 427/10; 427/8; 427/9; 118/712

(58) Field of Search .................. 427/8, 9, 10; 118/712

(56) References Cited

U.S. PATENT DOCUMENTS 3,338,736 A * 8/1967 Hain ........................ 428/409
4,121,459 A * 10/1978 MaCall et al. ............... 374/124

FOREIGN PATENT DOCUMENTS

| DE | 39 01 378 A1 | 8/1989 | .......... F26B/21/06 |
| DE | 195 00 073 C1 | 6/1996 | ........ G01N/25/200 |
| WO | WO 81/03704 | 12/1981 | .......... G01N/21/63 |

* cited by examiner

Primary Examiner—Katherine A. Bareford
(74) Attorney, Agent, or Firm—Cohen, Pontani, Lieberman & Pavane

(57) ABSTRACT

A method and apparatus for determining the profile of a coating layer of a paper or board web (2). The method comprises application of a coating slip to at least one surface of the web (2) at the coating head (1) of a coating machine, the measurement of the transverse temperature profile of the web (2) surface in at least a measurement point (7, 8) fitted after the coating head (1), and the determination of the profile of the web's (2) coating layer on the basis of the temperature profile measured in at least the measuring point (7, 8) fitted after the coating head (1), whereupon a change in the temperature of the web's (2) coating layer or in the difference of the temperature between the coating layer and the base web (2) is at least almost proportional to the change in the coat weight.

17 Claims, 1 Drawing Sheet

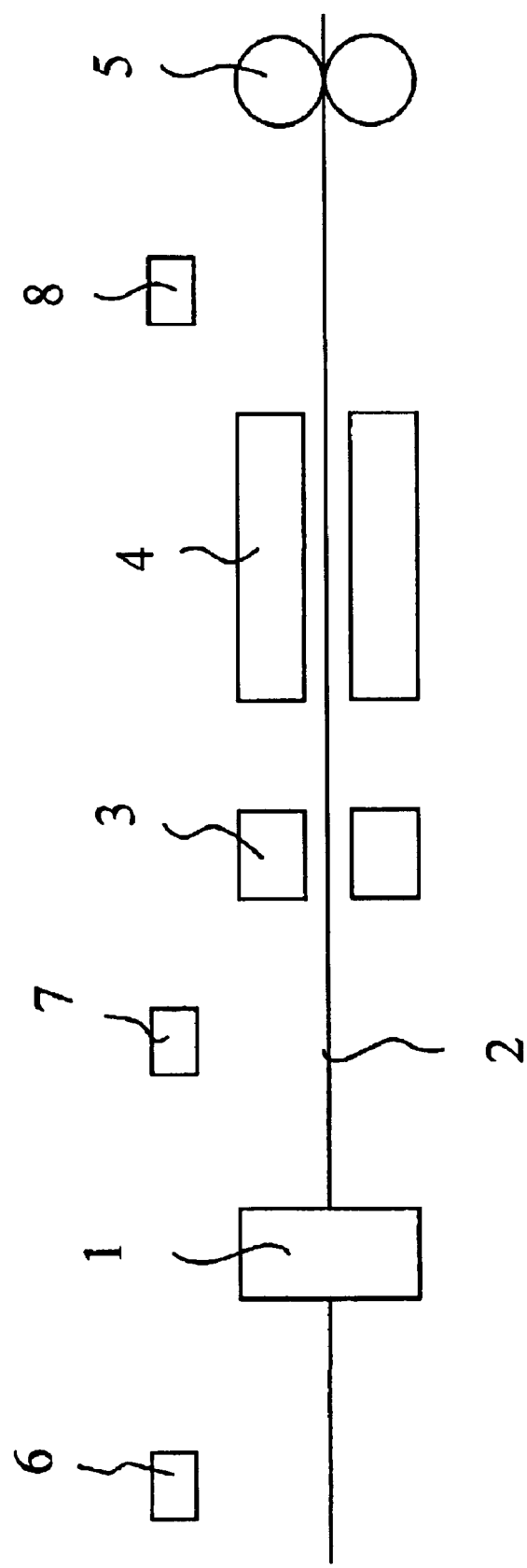

METHOD AND APPARATUS FOR DETERMINING THE PROFILE OF A COATING LAYER

PRIORITY CLAIM

This is a national stage of PCT application No. PCT/FI00/01083, filed on Dec. 11, 2000. Priority is claimed on that application and on patent application No. 19992652 filed in Finland on Dec. 9, 1999.

FIELD OF THE INVENTION

The present invention relates to a method and apparatus for determining the profile of a coating layer. A web is brought to a coating machine, and at the coating head of the machine, a coating slip is applied to a surface of the web. The profile of the coating layer applied to the web is determined.

BACKGROUND OF THE INVENTION

When coating paper or paperboard, a coating slip is first applied to a surface of a moving web, after which the surplus coating slip is removed and the surface of the coating layer is evened. Along with the coating slip, moisture enters the web; therefore, the excess moisture in the coating layer and the web is removed by drying. The coating machine can be located directly after the base paper machine, in which case the process is called on-machine coating. The coating machine can also be a separate device, to which the wound base paper rolls are taken and where they are unwound and coated, separately from the rest of the paper machine. This is called off-machine coating.

The web is dried by the drying part of the coating machine. The most common drier types include the infrared drier, the blast drier, and the drying cylinder. In the infrared drier, infrared radiation is emitted from the drier with the intention of inducing the highest intensity of radiation in wavelengths, where the absorption of radiation by water is high. In that case, the heating effect of the drier can be directed at the moisture among the coating as accurately as possible, whereupon the drying effect is the highest. In the blast drier, hot air is used to dry the web. In cylinder drying, for example, the web travels against a cylinder that is heated with steam, so that heat is transferred by convection from the cylinder surface to the web.

The drying of the coating slip layer can be divided into four different main stages. The first stage is a heating stage, during which the web temperature is quickly increased, generally, by the first infrared drier after the coating head. The web heats enough for the mass transfer, i.e., the rate of evaporation to be well balanced with the heat transfer. During the heating stage, moisture is absorbed from the coating layer into the base paper, the fibres of which swell up.

The second stage is the so-called stage of smooth evaporation, when all the heat that has been transferred to the web is consumed by drying. Generally, blast driers carry out the drying in the second stage, whereupon the temperature of the coating settles into balance with the moisture and temperature of the ambient air.

The third drying stage is the so-called first stage of decreasing evaporation, whereupon, when the surface of the coating layer dries, some of the capillaries that carry water to the surface are emptied and the evaporation is slowed down. In the third stage, the temperature of the coating starts a considerable increase.

The fourth and last drying stage is called the second stage of decreasing evaporation. As the capillaries no longer carry water to the surface, the surface of the coating layer is now completely dry. Therefore, the zone of evaporation moves inside the coating layer. The surface temperature of the coating layer increases very quickly. In the last drying stage, the coating is dry enough for the drying to be carried out by drying cylinders that touch the web.

When assessing the coating result, the coat weight is the most important indicator. The coat weight indicates the amount of dry matter of the coating slip on the paper in grams per square meter. The intention is to keep the profile of the coating layer both in the machine direction and the cross machine direction as even as possible with the aid of closed loop controls. In the machine direction, the profile of the coating layer is controlled, for example, by changing the load of the doctor blade or the doctor bar. In the cross machine direction of the web, the profile of the coating layer is controlled, for example, by locally changing the load of the doctor blade or the doctor bar in places, where the coat weight is too high or too low. The prerequisite for the profile control in both the machine direction and the cross machine direction is accurate measuring of the coat weight.

In measuring the coat weight, generally, measuring frames are used, comprising a slide provided with sensors, moving across the entire width of the paper web. The coat weight can be determined by measuring with sensors, for example, the absorption of beta radiation, the absorption or the fluorescence of X-radiation or the absorption of infrared radiation in the coating. Generally, the sensors measure one point only; therefore, the slide must cross the web to measure the profile of the coating layer along the entire width of the web.

The properties of the sensors set limitations to the speed of the measuring frame slides. The low power of the radiation sources in particular limits the slide speed in the case of sensors that are based on radiation. For the current sensors, the propagation speed of the slide is about 20 to 40 cm per second, whereupon it may take as much as one minute for the slide to cross a wide web, i.e., to perform one scanning. As the slide proceeds very slowly in the cross machine direction compared with the web speed in the machine direction, the method distorts the measuring results. While the sensor crosses the web once in the cross machine direction, the paper has travelled as much as over a kilometer in the machine direction. Normally, the transverse profile of the coating layer is calculated as the mean value of several scans, whereupon the adjustment of the transverse profile of the coating layer is slow and has an effect on long-term changes only.

Another problem in slow scanning is the effect of the differences of the coat weights in the machine direction on the transverse measurement of the coat weight. Any changes in the coating profile in the machine direction are serious interferences from the point of view of the transverse profile. Changes in the machine direction are often greater than any irregularities in the transverse profile, making the profile measurement unreliable, unless the changes are compensated for.

SUMMARY OF THE INVENTION

The goal of this invention is to provide an entirely novel method and arrangement for measuring the profile of a coating.

The invention is base on the fact that the profile of the coating applied to the web is indirectly determined or defined by measuring the surface temperature of the coating layer, for example, by a thermographic camera or an infrared pyrometer after the coating head. The measurement can be performed before the first drier or after any drier. Changes in the coat weight also cause changes in the temperature of the coating layer. When needed, the temperature of the base web can be measured before the coating head, whereupon the coating profile of the web can be determined with the aid of the changes in the difference of the temperature of the coating layer and the base web, or with the aid of heat balances. The method is well suited to determining the coating profile both in the machine and the cross machine direction.

The invention offers significant benefits.

The thermographic camera or the infrared pyrometer used as the measuring device has a large measuring angle, whereupon the surface temperature distribution of the coating and, on the basis of that, the profile of the coating layer can be quickly determined. Because of the quick determination of the coating layer profile, the coat weight to be applied at the coating head can be quickly adjusted. The invention can also be used to correct any profile defects in the base paper. In addition, the measuring equipment according to the invention is simple and easy to install both in new and existing coaters.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

In the following, the invention will be examined in more detail by making reference to the appended drawing, which is a schematic side view of the coating machine.

DETAILED DESCRIPTION OF THE PRESENTLY PREFERRED EMBODIMENTS

In connection with this invention, the concept "web surface" refers to the surface of the base web in places, which are not coated, and the surface of the coating layer on the coated places of the web.

The coating machine according to the drawing comprises a coating head 1, from where the coating slip is applied to the web 2. After the coating head 1, the web 2 is taken to an infrared drier 3, where the temperature of the web 2 is increased by using infrared radiation. During the heating stage by using the infrared drier 3, the temperature of the web 2 is increased quickly, whereupon the web 2 is heated enough for the mass transfer, i.e., the amount of evaporation to be in balance with the heat transfer. Generally, the temperature of the web 2 is increased to about 60° C. by using the infrared drier 3. During the heating stage, moisture is absorbed from the coating layer into the base web, the fibres of which swell up.

After the infrared drier 3, the web 2 is taken to a blast drier 4, where the web 2 is heated by blowing air on both sides of the web 2. At the blast drier 4, drying the web 2 is transferred to a second stage, whereupon all the heat transferred to the web 2 is consumed by drying and the temperature of the coating settles into balance with the humidity and the temperature of the ambient air. Typically, the temperature of the coating in the second stage is about 60 to 65° C.

As the surface of the coating layer dries, some of the capillaries that carry water to the surface are emptied and the evaporation of the moisture is slowed down, whereupon a third drying stage is reached. In the third stage, the temperature of the coating starts a substantial increase. In the third stage, the temperature of the web 2 typically increases to more than 65° C. and the dry content to more than 78%.

After the blast drier 4, the coating layer of the web 2 is so dry that drying can be performed by a cylindrical drier 5 that touches the web, the web 2 travelling through the drier between cylinders that are heated with steam, for example, whereupon heat is convectively transferred from the cylinders to the web 2. The web 2 now dries in a fourth stage, whereupon the capillaries of the coating layer no longer carry water to the surface, and the zone of evaporation moves inside the coating. The temperature of the coating increases very rapidly. In the fourth stage, the dry content of the coating is typically more than 85% and the temperature more than 70° C.

The surface temperature of the coating layer applied to the web 2 in the lateral direction is measured at a measuring point 7 located after the coating head 1 and before the first drier 3. In addition, or instead, the temperature of the coating layer can also be measured at a measuring point located after any of the driers 3, 4, and 5, preferably at a measuring point 8 located after the blast drier 4, whereupon the temperature of the coating is more than 60° C., and it has been observed that the temperature of the coating and the coat weight are better correlated with each other than after the infrared drier 3 or the cylindrical drier 5. By locating a measuring point both before the drier and after the drier, the operation of the drier can be monitored.

If the temperature profile of the web 2 is sufficiently even before it arrives at the coating head 1, the profile of the coating layer of the web 2 in the machine or cross machine direction can be defined on the basis of the temperature profile measured at the measuring point 7, 8 located after the coating head 1. When needed, the temperature profile can be measured on both sides of the web 2.

The temperature differences measured immediately after the coating head 1 are caused by the temperature differences of the coating slip and the base web 2 and, to a certain extent, by the coating method used. In off-machine coaters, the temperature of the coating slip to be applied to the web is generally higher than that of the base web, whereupon in places, where the temperature is high, the layer of coating slip is thick. Correspondingly, in on-machine coaters, where the temperature of the base web can be higher than that of the coating slip to be applied to the web, the coating layer is thick in places, where its temperature is low.

The fluctuations in the temperature visible in the various drying stages are mainly caused by the differences of humidity in the coating layer. The differences of humidity in the coated web 2 are mainly caused by the differences of the coat weight, as the content of water in the coating slip is typically about 30 to 40%. When the coating layer is dried, heat energy is brought to the web, whereupon the differences of humidity cause differences of the temperature. The lower the measured temperature, the thicker the coating layer in the measured place, as evaporating the water from the coating slip requires a lot of energy.

By measuring the transverse temperature profile of the coating layer of the web 2 after the coating head 1, the profile of the coating layer can be determined on the basis of the measured temperature profile, whereupon a change in the temperature of the coating layer is at least almost proportional to the change in the coat weight in said place.

In on-machine coaters in particular, the temperature of the base web 2 coming to the coating head 1 is not necessarily sufficiently even in the cross direction, whereupon the differences of the temperature may complicate the determination of the coat weight. In that case, the temperature profile of the surface of the base web 2 must also be measured at the measuring point 6 before the coating head 1, so that the effect of the temperature fluctuations of the base web 2 on the temperature of the coating layer measured after the coating head 1 can be eliminated. The coating profile can now be determined on the bases of the measured temperature profiles, so that a change in the difference of the temperature between the measuring point 7, 8 fitted after the coating head 1 and the measuring point 6 fitted before the coating head 1 is at least almost proportional to the change in the coat weight.

The temperature can be measured in the measuring points 6, 7, 8, for example, by using an infrared pyrometer or a thermographic camera. The thermographic camera is a more accurate measuring device than the infrared pyrometer. One or more measuring devices can be used in the measuring points 6, 7, 8. The measuring angle of the thermographic camera is about 90°, so that one thermographic camera can be used to measure, for example, a 10 meters wide web 2 at a distance of about 5 meters from the centre line of the web 2.

If the temperature of the web 2 is measured both before and after the coating head 1, the coat weight of the web 2 can be defined with the aid of heat balances. The coat weight can be solved by the balance equation:

$$CW = \frac{BW \cdot c_{base}(T_{web} - T_{base})}{c_{colour}(T_{colour} - T_{web})}, \quad \text{wherein}$$

CW is the coat weight [g/m$^2$],
$C_{colour}$ is the specific heat capacity of the coating colour [J/(kg·K)],
$T_{colour}$ is the temperature of the coating colour before coating [K],
BW is the square weight of the base paper [g/m$^2$],
$C_{base}$ is the specific heat capacity of the base paper [J/(kg·K)],
$T_{base}$ is the temperature of the base paper before coating [K], and
$T_{web}$ is the temperature of the paper web after coating [K].

Furthermore, various correction coefficients can be used in the above equation, taking into consideration the effect of different unwanted factors on the calculation result. One such unwanted factor is, for example, the cooling of the web 2 of the coating head 1 in the subsequent free draft before the measuring point 7.

The solution according to the invention can also be used in the on-line calendaring of the web. The moisture content of the web's coating layer, which is brought to the calender, must not be too high, as in that case the coating may adhere to the calender rolls. The moisture content of the coating varies when the coat weight changes. Small-scale changes in the coat weight are caused by changes in the formation and the porosity of the base web that is brought to the coater. If the web temperature is measured by a thermographic camera or an infrared pyrometer before calendaring, the coat weight and the moisture content of the coating layer can be determined on the basis of the measurement results. On the basis of the measurement results, the precoater, the size press or other device that changes the bite and the porosity of the web is adjusted, so that the moisture of the web coating coming to the calender is low enough not to adhere to the calender rolls.

Thus, while there have been shown and described and pointed out fundamental novel features of the present invention as applied to a preferred embodiment thereof, it will be understood that various omissions and substitutions and changes in the form and details of the devices described and illustrated, and in their operation, and of the methods described may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A method for determining a profile of a coating layer applied to at least one surface of a paper or board web, comprising:

applying a coating layer to at least one surface of a paper or board web;

measuring a first transverse temperature profile of a surface of the coated web, wherein the measuring of the first transverse temperature profile takes place at a first measuring point after the coating layer has been applied to the web;

determining a profile of the applied coating layer based upon the measured first transverse temperature profile; and measuring a second transverse temperature profile of the surface of the web, wherein the measuring of the second transverse temperature profile takes place at a second measuring point before the coating layer has been applied to the web, wherein determining the profile of the applied coating layer comprises comparing the measured first transverse temperature profile to the measured second transverse temperature profile to determine a change in a transverse temperature profile, wherein a coat weight of the applied coating layer is substantially proportional to the change in the transverse temperature profile.

2. The method of claim 1, wherein the first measuring point is located after a drier in which the coated web is at least partially dried.

3. The method of claim 1, wherein the profile of the applied coating layer is determined in a direction across a width of the web being transverse to the direction of travel of the web.

4. The method of claim 1, wherein the profile of the applied coating layer is determined in a direction along a length of the web being in a direction of travel of the web.

5. The method of claim 1, wherein the first measuring point is located before a drier in which the coated web is at least partially dried.

6. The method of claim 1, wherein the first measuring point is located after a blast drier in which the coated web is at least partially dried.

7. The method of claim 1, wherein at least one temperature profile of the surface of the web is measured with at least one infrared pyrometer.

8. The method of claim 7, wherein at least one temperature profile of the surface of the web is measured with at least one thermographic camera.

9. The method of claim 1, wherein at least one temperature profile of the surface of the web is measured with at least one thermographic camera.

10. A method for determining a profile of a coating layer applied to at least one surface of a paper or board web, comprising:
   applying a coating layer to at least one surface of a paper or board web;
   measuring a first transverse temperature profile of a surface of the coated web with at least one thermographic camera, wherein the measuring of the first transverse temperature profile takes place at a first measuring point after the coating layer has been applied to the web; and
   determining a profile of the applied coating layer based upon the measured first transverse temperature profile.

11. An apparatus for determining a profile of a coating layer applied to at least one surface of a paper or board web, comprising:
   a coater means for applying a coating layer to at least one surface of a paper or board web;
   a first measuring means for measuring a first transverse temperature profile of a surface of the coated web, wherein the first measuring means is positioned at a first measuring point after the coating layer has been applied to the web by the coater means;
   a means for determining a profile of the applied coating layer based upon the measured first transverse temperature profile; and
   a second measuring means for measuring a second transverse temperature profile of the surface of the web, wherein the second measuring means is positioned at a second measuring point before the coating layer has been applied to the web by the coater means,
   wherein the means for determining the profile of the applied coating layer compares the measured first transverse temperature profile to the measured second transverse temperature profile to determine a change in transverse temperature profile, wherein a coat weight of the applied coating layer is substantially proportional to a change between the measured first transverse temperature profile and the measured second transverse temperature profile.

12. The apparatus of claim 11, wherein said first measuring means comprises at least one infrared pyrometer.

13. The apparatus of claim 12, wherein said first measuring means comprises at least one thermographic camera.

14. The apparatus of claim 11, wherein at least one of said first and second measuring means comprises at least one infrared pyrometer.

15. The apparatus of claim 14, wherein at least one of said first and second measuring means comprises at least one thermographic camera.

16. The apparatus of claim 11, wherein said first measuring means comprises at least one thermographic camera.

17. An apparatus for determining a profile of a coating layer applied to at least one surface of a paper or board web, comprising:
   a coater means for applying a coating layer to at least one surface of a paper or board web;
   at least one thermographic camera for measuring a first transverse temperature profile of a surface of the coated web, wherein the at least one thermographic camera is positioned at a first measuring point after the coating layer has been applied to the web by the coater means; and
   a means for determining a profile of the applied coating layer based upon the measured first transverse temperature profile.

* * * * *